(12) United States Patent
Kang et al.

(10) Patent No.: US 8,124,283 B2
(45) Date of Patent: Feb. 28, 2012

(54) CYCLIC SILOXANE-BASED COMPOUNDS AND SOLID POLYMER ELECTROLYTE COMPOSITION CONTAINING THE SAME AS A CROSSLINKING AGENT

(75) Inventors: Yongku Kang, Daejeon (KR); Changjin Lee, Daejeon (KR); Jun Kyoung Lee, Daejeon (KR); Joung In Lee, Chungcheongnam-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 1129 days.

(21) Appl. No.: 11/886,211

(22) PCT Filed: Mar. 20, 2006

(86) PCT No.: PCT/KR2006/001011
§ 371 (c)(1),
(2), (4) Date: Sep. 12, 2007

(87) PCT Pub. No.: WO2006/101328
PCT Pub. Date: Sep. 28, 2006

(65) Prior Publication Data
US 2008/0171267 A1    Jul. 17, 2008

(30) Foreign Application Priority Data
Mar. 23, 2005  (KR) .................. 10-2005-0024250

(51) Int. Cl.
*H01M 6/18* (2006.01)
(52) U.S. Cl. ........ 429/313; 429/311; 429/310; 429/309; 429/306; 429/304
(58) Field of Classification Search .................. 429/313, 429/311, 310, 309, 306, 304
See application file for complete search history.

(56) References Cited

U.S. PATENT DOCUMENTS

| | | | |
|---|---|---|---|
| 4,673,718 | A | 6/1987 | Ryntz et al. |
| 4,766,185 | A | 8/1988 | Ryntz et al. |
| 4,830,939 | A | 5/1989 | Lee et al. |
| 5,227,043 | A | 7/1993 | Shakushiro et al. |
| 5,440,011 | A | 8/1995 | Laine |
| 5,719,230 | A | 2/1998 | Ando et al. |
| 2003/0134968 | A1 | 7/2003 | Kang et al. |

FOREIGN PATENT DOCUMENTS

| | | |
|---|---|---|
| JP | 04-056002 | 2/1992 |
| JP | 05-290616 | 11/1993 |
| JP | 09-296045 | 11/1997 |
| KR | 1020030040618 A | 5/2003 |
| KR | 1020050116475 A | 12/2005 |

*Primary Examiner* — Helen O Conley
(74) *Attorney, Agent, or Firm* — Frommer Lawrence & Haug LLP; Ronald R Santucci (57) ABSTRACT

The present invention relates to a cyclic siloxane-based compound and a solid polymer electrolyte composition containing the same as a crosslinking agent. The cyclic siloxane-based compound having a novel structure in which polyalkylene oxide acrylate groups are introduced into a cyclic siloxane compound and a solid polymer electrolyte composition containing the cyclic siloxane-based compound as a crosslinking agent along with other electrolyte components such as a plasticizer, lithium salt and a curing initiator. Since the solid polymer electrolyte composition of the present invention improves ion conductivity and electrochemical stability at room temperature, it can be useful as polymer electrolyte for electrolyte films, small-sized to high-capacity lithium-polymer secondary batteries, etc. Also, physical properties of the polymer electrolyte can be controlled easily by controlling the length of the polyalkylene oxide group in the cyclic siloxane-based crosslinking agent.

4 Claims, 2 Drawing Sheets

CYCLIC SILOXANE-BASED COMPOUNDS AND SOLID POLYMER ELECTROLYTE COMPOSITION CONTAINING THE SAME AS A CROSSLINKING AGENT

This application is a 371 of PCT/KR2006/001011 filed on Mar. 20, 2006, published on Sep. 28, 2006 under publication number WO 2006/101328 A1 which claims priority benefits from Korean Patent Application No. 10-2005-0024250 filed Mar. 23, 2005, the disclosure of which is hereby incorporated by reference.

TECHNICAL FIELD

The present invention relates to a cyclic siloxane-based compound and a solid polymer electrolyte composition containing the same as a crosslinking agent. More particularly, the present invention relates to a cyclic siloxane-based compound having a novel structure in which polyalkylene oxide acrylate groups are introduced into a cyclic siloxane compound and a solid polymer electrolyte composition containing the cyclic siloxane-based compound as a crosslinking agent along with other electrolyte components such as a plasticizer, lithium salt and a curing initiator. Since the solid polymer electrolyte composition of the present invention improves ion conductivity and electrochemical stability at room temperature, it can be useful as polymer electrolyte for electrolyte thin film batteries, small-sized to high-capacity lithium-polymer secondary batteries, etc. Further, mechanical and electrochemical properties of polymer electrolyte can be controlled easily by changing the length of the polyalkylene oxide group in the cyclic siloxane-based crosslinking agent.

BACKGROUND ART

Electrochemical devices using liquid electrolytes have a safety problem because of the possibility of leakage and explosion. Electrochemical devices using polymer electrolytes were developed to solve this problem. For example, a lithium-polymer battery is superior in safety and also provides excellent charge-discharge efficiency. In addition, various designs are possible and the cell size can be reduced because the electrolyte can be obtained in a thin film.

Particularly, solid polymer electrolytes which comprise polyalkylene oxide (PAO)-based and gel-type polymer electrolyte containing organic liquid electrolytes were viewed as candidates of polymer electrolytes of lithium secondary batteries. Efforts have been made to improve conductivity of polymer electrolytes by adding low-molecular-weight polyalkylene oxides or organic solvents as a plasticizer. However, physical properties of polymer electrolytes deteriorate significantly or a stable gel may not be obtained if the content of a plasticizer increases.

A method to overcome the above-identified problem was disclosed, wherein a crosslinked polymer electrolyte was prepared by curing a composition containing polyalkylene glycol compound having a chemically crosslinkable group, an ion-conductive liquid and an electrolyte salt through UV radiation or electron beam radiation [U.S. Pat. No. 4,830,939, *J. Electrochemm. Soc.,* 145, 1521 (1998)].

Recently, researches have been conducted using polysiloxane-based polymers, which have good flexibility and low glass transition temperature, and are thus expected to be capable of improving molecular chain movement, as the backbone of polyalkylene oxide-based, crosslinked polymer electrolytes [*Macromolecules,* 36 (2003), 9176, U.S. Pat. Nos. 4,673,718, 4,766,185, 5,227,043 and 5,440,011, Japanese Patent Laid-Open No. Hei 5-290616]. However, the polysiloxane-based polymer electrolytes are not suitable for use in lithium cells to be operated at room temperature, because they have poor mechanical properties and very low ion conductivity of $10^{-4}$ S/cm.

To solve the above problems, the present inventors developed a technique of partially enhancing mechanical properties by using a novel crosslinking agent obtained by introducing an acryl group, which is crosslinkable by heat or light, at both ends or side chain of a methylsiloxane polymer having polyalkylene oxide branches and acquired a patent for the technique [Korean Patent No. 419864, Korean Patent Application No. 2004-41502]. Although this polymer electrolyte composition was a fairly innovative one, it had a drawback that mechanical properties of the electrolyte cannot be controlled as required. This is due to the inability to control the exact control of degree of crosslinking because the content of the acryl group, which determines the degree of crosslinking, is dependent on the molecular weight of the polymer.

While endeavoring to solve the aforementioned problems, the inventors of the present invention discovered that a cyclic siloxane-based compound, when introduced with polyalkylene oxide acrylate groups, becomes easily crosslinkable and also its degree of crosslinking can be easily controlled. Further, if the above compound is used as a crosslinking agent of the polymer electrolyte it enables to control mechanical properties of the polymer electrolyte.

Therefore, in an embodiment of the present invention, there is provided a cyclic siloxane-based compound into which polyalkylene oxide acrylate groups are introduced.

In another embodiment of the present invention, there is provided a solid polymer electrolyte composition containing the cyclic siloxane-based compound as a crosslinking agent.

In still another embodiment of the present invention, there is provided a use of the solid polymer electrolyte composition as polymer electrolyte of electrolyte films and lithium-polymer secondary batteries.

DISCLOSURE OF THE INVENTION

The present invention relates to a cyclic siloxane-based compound wherein a polyalkylene oxide acrylate is introduced into a cyclic siloxane compound, which is represented by the formula (1) below:

(1)

wherein $R_1$, $R_2$ and $R_3$ are independently hydrogen or $C_1$-$C_6$ alkyl, and n and m are independently an integer of from 0 to 20 (except when both n and m are 0).

Hereunder is given a detailed description of the present invention.

The present invention relates to a readily crosslinkable cyclic siloxane-based compound prepared by introducing polyalkylene oxide acrylate groups into a cyclic siloxane monomer and a solid polymer electrolyte composition containing the cyclic siloxane-based compound as a crosslinking agent, which has significantly improved compatibility with other electrolyte components such as a plasticizer, lithium salt and photo- or thermal-curing initiator and improved ion conductivity and electrochemical stability at room temperature.

The cyclic siloxane-based compound represented by the formula (1) is prepared by the steps of:

reacting tetramethylcyclotetrasiloxane (D4H) represented by the formula (2) below with an allyl alcohol represented by the formula (3) below in the presence of a platinum catalyst to obtain a D4-2,4,6,8-tetra(alkoxyalcohol) represented by the formula (4) below; and reacting the D4-2,4,6,8-tetra(alkoxyalcohol) represented by the formula (4) with acryloyl chloride represented by the formula (5) below in the presence of an amine base to obtain the cyclic siloxane-based compound represented by the formula (1):

Scheme 1 where $R_1$, $R_2$, $R_3$, n and m are the same as defined above.

The allyl alcohol represented by the formula (3), which is used as a starting material in Scheme 1, is prepared by reacting a polyoxyalkylene alcohol with allyl bromide in the presence of a base.

The present invention also relates to a solid polymer electrolyte containing the cyclic siloxane-based compound represented by the formula (1) as a crosslinking agent. The cyclic siloxane-based compound of the present invention can be used as a crosslinking agent for a variety of purposes, including improvement of mechanical strength such as hardness and elasticity of polymer materials like rubber, plastics, etc. and improvement of chemical or electrochemical stability. Preferably, the cyclic siloxane-based compound of the present invention can be used as a component for a polymer electrolyte composition for electrolyte films and small-sized to high-capacity lithium-polymer secondary batteries as a crosslinking agent.

Thus, the present invention relates to a use of the electrolyte composition containing the cyclic siloxane-based compound represented by the formula (1) as a crosslinking agent for polymer electrolyte of electrolyte films and lithium-polymer secondary batteries.

The solid polymer electrolyte composition of the present invention may comprise a crosslinking agent, a plasticizer, lithium salt and a curing initiator.

For the crosslinking agent, the cyclic siloxane-based compound represented by the formula (1) is used. Because the cyclic siloxane-based compound has polyalkylene oxide acrylate groups at the side chain, it increases compatibility with a plasticizer, which is added to improve ion conductivity of the electrolyte. Also, the polymer electrolyte can have a 3-dimensional network structure because of the acryl groups present in the molecules. In addition, it is possible to control physical properties of the electrolyte by changing the length of the polyalkylene oxide chain.

The crosslinking agent may be contained in the amount of 0.1-95 wt %, preferably 0.5-80 wt %, more preferably 0.5-60 wt %.

The plasticizer is added to improve ion conductivity by promoting dissociation of the lithium salt. As a plasticizer, at least one compound selected from the group consisting of polyalkylene glycol dialkyl ether represented by the formula (2) below, polymethyl(polyalkylene oxide)siloxane represented by the formula (3) below, a methyl(polyalkylene oxide)cyclic siloxane represented by the formula (4) below and a non-aqueous polar solvent may be used.

In the above formulas (2), (3) and (4), $R_4$ and $R_5$ are independently $C_1$-$C_{10}$ linear or branched alkyl, $R_6$, $R_7$ and $R_8$ are independently hydrogen or methyl, o, p and q are independently an integer of from 0 to 20 (except when both p and q are 0) and x is an integer of from 1 to 1000.

Examples of the polyalkylene glycol dialkyl ether that can be used as the plasticizer in the present invention are polyethylene glycol dimethyl ether, polyethylene glycol diethyl ether, polyethylene glycol dipropyl ether, polyethylene glycol dibutyl ether, polyethylene glycol diglycidyl ether, polypropylene glycol dimethyl ether, polypropylene glycol diglycidyl ether, polypropylene glycol/polyethylene glycol copolymer having a dibutyl ether terminal group and polyethylene glycol/polypropylene glycol/polyethylene glycol block copolymer having a dibutyl ether terminal group. Examples of the non-aqueous polar solvent are ethylene carbonate, propylene carbonate, butylene carbonate, dimethyl carbonate, tetrahydrofuran, 2-methyltetrahydrofuran, 1,3-dioxirane, 4,4-dimethyl-1,3-dioxirane, γ-butyrolactone, acetonitrile, etc.

The content of a plasticizer in the electrolyte is proportionally related to the ion conductivity of the polymer electrolyte. However, if its content is excessive, the mechanical property of the resulting polymer electrolyte will be drastically deteriorated and it is difficult to obtain a thin film. Thus, the plasticizer is preferably contained in the amount of 0.1-98 wt %, more preferably 30-97 wt %.

The lithium salt may be any one commonly used in the production of polymer electrolytes. For example, $LiClO_4$, $LiCF_3SO_3$, $LiBF_4$, $LiPF_6$, $LiAsF_6$, $Li(CF_3SO_2)_2N$, etc., may be used.

The lithium salt is preferably contained in the amount of 3-40 wt %, more preferably 5-25 wt %, but the content may be adjusted, if deemed necessary.

The curing initiator may be either a photo-curing type or a thermal-curing type. Examples of the photo-curing initiator are ethyl benzoin ether, isopropyl benzoin ether, α-methyl benzoin ethyl ether, benzoin phenyl ether, α-acyloxime ester, α,α-diethoxyacetophenone, 1,1-dichloroacetophenone, 2-hydroxy-2-methyl-1-phenylpropan-1-one (Darocur 1173, Ciba-Geigy), 1-hydroxycyclohexyl phenyl ketone (Irgacure 184, Ciba-Geigy), Darocur 1116, Irgacure 907, anthraquinone, 2-ethylanthraquinone, 2-chloroanthraquinone, thioxanthone, isopropylthioxanthone, chlorothioxanthone, benzophenone, p-chlorobenzophenone, benzyl benzoate, benzoyl benzoate, Michler's ketone, etc. Examples of the thermal-curing initiator are azoisobutyronitriles, peroxides, etc.

The curing initiator may be contained in the amount of 0.1-5 wt %. The content may be adjusted depending on the mixing ratio of oligomers or polymers that are added together.

The present invention provides a use of the solid polymer electrolyte composition as polymer electrolyte for electrolyte films and lithium-polymer secondary batteries.

A process of preparing an electrolyte film is described as an example of the use of the solid polymer electrolyte composition. First, a plasticizer and lithium salt are mixed to adequate proportion and stirred to obtain a solution. Then, a crosslinking agent and curing initiator are added in this order and the resulting mixture solution is stirred to obtain a composition solution for preparing a solid polymer electrolyte. The resulting solution is coated on a support, such as a glass plate, polyethylene, polyvinyl polymers, Mylar film and cell electrode, to an adequate thickness and cured by radiating electron beam, UV or γ-ray or by heating. Alternatively, a solid polymer electrolyte film having a uniform thickness may be prepared by coating the composition solution on a support, fixing spacers at either end of the support for thickness control and covering it with another support and then curing with radiation or heating.

A process of preparing a polymer electrolyte for lithium-polymer secondary batteries is described as another example of the use of the solid polymer electrolyte composition.

A lithium-polymer secondary battery comprise an anode, an electrolyte and a cathode. Lithium metal oxides like $LiCoO_2$, $LiNiO_2$, etc. are commonly used as anode and carbon materials like graphite or coke, e.g., MCMB and MPCF, or metallic lithium are used as cathode. In the present invention, an electrolyte solution is prepared by mixing a crosslinking agent, a plasticizer, a lithium salt and a curing initiator and is poured onto a substrate to obtain a film having a wanted thickness. The film is cured for a predetermined time to obtain a polymer electrolyte film. In addition to the above-mentioned method, other commonly used methods can be applied in the preparation of a lithium-polymer secondary cell.

The present invention is advantageous in that, by using a cyclic siloxane-based compound as a crosslinking agent of a solid polymer electrolyte composition, physical properties of the electrolyte, including mechanical strength and ion conductivity, are improved significantly.

BEST MODE FOR CARRYING OUT THE INVENTION

Hereunder is given a more detailed description of the present invention. However, it will be appreciated that those skilled in the art, in consideration of this disclosure, may make modifications and improvements within the spirit and scope of the present invention.

PREPARATION EXAMPLES

Synthesis of Poly(Ethylene Glycol) Monoallyl Alcohols

[formula (3)]

Preparation Example 1

Synthesis of di(ethylene glycol)monoallyl alcohol (ADEGA)

In a 1000 mL, 3-neck round-bottomed flask equipped with a stirrer, a thermometer and a dropping apparatus, 18.84 g (0.47 mol) of NaOH and 50 g (0.47 mol) of di(ethylene glycol) (DEG, n=2) were added to THF (550 mL), which had been dried with sodium. Excess allyl bromide [57 g (0.47 mol)] was added under nitrogen atmosphere and refluxed for 12 hours. When the reaction was completed, the remaining NaOH and NaBr produced thereof were filtered out and THF was removed under reduced pressure. The remainder was dissolved with a 5 wt % sodium hydroxide aqueous solution and extracted 3 times with hexane. The aqueous layer was extracted 3 times with chloroform or dichloromethane. The resulting organic layer was dried with $MgSO_4$ and then dried under vacuum to obtain 45 g of di(ethylene glycol) monoallyl alcohol (ADEGA, n=2, $M_w$=146) (yield=66%).

$^1$H-NMR (300 MHz, $CDCl_3$): ppm 3.07 (s, 1H), 3.35-3.69 (m, 8H), 4.02 (d, 2H), 5.25 (m, 2H), 5.90 (m, 1H)

Preparation Example 2

Synthesis of tri(ethylene glycol)monoallyl alcohol (ATEGA)

90 g of tri(ethylene glycol) monoallyl alcohol (ATEGA n=3, $M_w$=190) was prepared in the same manner as in Preparation Example 1, except that 100 g of tri(ethylene glycol) (TEG, n=3), 26.64 g of NaOH and 80.56 g of allyl bromide were used (yield=71%).

$^1$H-NMR (300 MHz, CDCl$_3$): ppm 3.07 (s, 1H), 3.38-3.67 (m, 12H), 4.02 (d, 2H), 5.25 (m, 2H), 5.90 (m, 1H)

Preparation Example 3

Synthesis of tetra(ethylene glycol)monoallyl alcohol (ATTEGA)

60 g of tetra(ethylene glycol) monoallyl alcohol (ATTEGA, n=4, M$_w$=234) was prepared in the same manner as in Preparation Example 1, except that 70 g of tetra(ethylene glycol) (TEG, n=4), 14.42 g of NaOH and 43.61 g of allyl bromide were used (yield=70%).

$^1$H-NMR (300 MHz, CDCl$_3$): ppm 3.07 (s, 1H), 3.36-3.69 (m, 16H), 4.03 (d, 2H), 5.25 (m, 2H), 5.90 (m, 1H)

Preparation Example 4

Synthesis of penta(ethylene glycol)monoallyl alcohol (APEGA)

75 g of penta(ethylene glycol) monoallyl alcohol (APEGA, n=5, M$_w$=278) was prepared in the same manner as in Preparation Example 1, except that 95 g of penta(ethylene glycol) (PEG, n=5), 16 g of NaOH and 48.39 g of allyl bromide were used (yield=67%).

$^1$H-NMR (300 MHz, CDCl$_3$): ppm 3.07 (s, 1H), 3.34-3.67 (m, 20H), 4.03 (d, 2H), 5.27 (m, 2H), 5.92 (m, 1H)

Examples

Synthesis of Cyclic Methyl Siloxane Compounds
[Formula (1)]

Example 1

Synthesis of tetramethyl tetra(ethoxyacrylate)cyclotetrasiloxane (D4A, n=1)

In 100 mL of toluene was dissolved 2,4,6,8-tetramethylcyclotetrasiloxane (D4H) (10 g, 0.0426 mol). Then, Pt(0) catalyst was added and the allyloxyethanol (AOE, 18.68 g, 0.17 mol) dissolved in 150 mL of toluene was added dropwise. After 12 hours of reflux at 100° C. under nitrogen atmosphere, the mixture was cooled to room temperature and stirring was performed after adding activated carbon. About 24 g of D4-2,4,6,8-tetra(ethoxyethanol) (D4OE, n=1) was obtained after filtration and evaporation under reduced pressure (yield=90%).

$^1$H-NMR (300 MHz, CDCl$_3$): ppm 0.00 (s, 3H), 0.39-0.43 (m, 2H), 1.50-1.62 (m, 2H), 2.6 (s, 1H), 3.31-3.47 (m, 4H), 3.65 (d, 2H)

6 g (0.00925 mol) of thus obtained D4OE and 4.5 g (0.037 mol) of triethylamine were dissolved in 100 mL of CHCl$_3$ in a 3-neck round-bottomed flask. Then, 4 g (0.037 mol) of acryloyl chloride dissolved in 100 mL of CHCl$_3$ was added dropwise while stirring at 0° C. After about 12 hours of reaction, the precipitate was removed and distillation was performed under reduced pressure. The resulting yellow viscous liquid product was dissolved in chloroform and extracted several times with water. The chloroform layer was separated and dried with MgSO$_4$. About 6 g of tetramethyl tetra(ethoxyacrylate) cyclotetrasiloxane (D4A, n=1) was obtained by evaporation under reduced pressure (yield=75%).

$^1$H-NMR (300 MHz, CDCl$_3$): ppm 0.00 (s, 3H), 0.39-0.53 (m, 2H), 1.5-1.6 (m, 2H), 3.25-3.43 (m, 2H), 3.52-3.67 (m, 2H), 4.17-4.3 (m, 2H), 5.7-5.85 (d, 1H), 6.0-6.2 (m, 1H), 6.3-6.45 (d, 1H).

Example 2

Synthesis of tetramethyl tetra(ethoxyacrylate)cyclotetrasiloxane (D4A, n=2)

15 g of D4-2,4,6,8-tetra(ethoxyethanol) (D4OE, n=2) was prepared in the same manner as in Example 1, except that 6 g of 2,4,6,8-tetramethylcyclotetrasiloxane (D4H) and 14.569 g of di(ethylene glycol) monoallyl alcohol were used (yield=73.1%).

$^1$H-NMR (300 MHz, CDCl$_3$): ppm 0.00 (s, 3H), 0.39-0.43 (m, 2H), 1.50-1.62 (m, 2H), 2.7 (s, 1H), 3.31-3.47 (m, 2H), 3.5-3.8 (d, 8H)

13 g of tetramethyl tetra(ethoxyacrylate) cyclotetrasiloxane (D4A, n=2) was prepared in the same manner as in Example 1, except that 15 g of D4-2,4,6,8-tetra(ethoxyethanol) (D4OE, n=2) and 6.5 g of acryloyl chloride were used (yield=68.8%).

$^1$H-NMR (300 MHz, CDCl$_3$): ppm 0.00 (s, 3H), 0.39-0.53 (m, 2H), 1.5-1.6 (m, 2H), 3.25-3.43 (m, 2H), 3.52-3.78 (m, 6H), 4.17-4.3 (m, 2H), 5.7-5.85 (d, 1H), 6.0-6.2 (m, 1H), 6.3-6.45 (d, 1H).

Example 3

Synthesis of tetramethyl tetra(ethoxyacrylate)cyclotetrasiloxane (D4A, n=3)

18 g of D4-2,4,6,8-tetra(ethoxyethanol) (D4OE, n=3) was prepared in the same manner as in Example 1, except that 5 g of 2,4,6,8-tetramethylcyclotetrasiloxane (D4H) and 15.2 g of tri(ethylene glycol) monoallyl alcohol were used (yield=90%).

$^1$H-NMR (300 MHz, CDCl$_3$): ppm 0.00 (s, 3H), 0.39-0.43 (m, 2H), 1.50-1.62 (m, 2H), 2.7 (s, 1H), 3.31-3.47 (m, 2H), 3.5-3.8 (d, 12H)

10 g of tetramethyl tetra(ethoxyacrylate) cyclotetrasiloxane (D4A, n=3) was prepared in the same manner as in Example 1, except that 13.87 g of D4-2,4,6,8-tetra(ethoxyethanol) (D4OE, n=3) and 5.27 g of acryloyl chloride were used (yield=63.3%).

$^1$H-NMR (300 MHz, CDCl$_3$): ppm 0.00 (s, 3H), 0.39-0.53 (m, 2H), 1.5-1.6 (m, 2H), 3.25-3.43 (m, 2H), 3.52-3.78 (m, 10H), 4.17-4.3 (m, 2H), 5.7-5.85 (d, 1H), 6.0-6.2 (m, 1H), 6.3-6.45 (d, 1H).

Example 4

Synthesis of tetramethyl tetra(ethoxyacrylate)cyclotetrasiloxane (D4A, n=4)

14 g of D4-2,4,6,8-tetra(ethoxyethanol) (D4OE, n=4) was prepared in the same manner as in Example 1, except that 4 g of 2,4,6,8-tetramethylcyclotetrasiloxane (D4H) and 15.95 g of tetra(ethylene glycol) monoallyl alcohol were used (yield=84%).

$^1$H-NMR (300 MHz, CDCl$_3$): ppm 0.00 (s, 3H), 0.39-0.43 (m, 2H), 1.50-1.62 (m, 2H), 2.7 (s, 1H), 3.31-3.47 (m, 2H), 3.5-3.8 (d, 16H)

14.5 g of tetramethyl tetra(ethoxyacrylate) cyclotetrasiloxane (D4A, n=4) was prepared in the same manner as in Example 1, except that 17.24 g of D4-2,4,6,8-tetra(ethoxyethanol) (D4OE, n=4) and 6.27 g of acryloyl chloride were used (yield=65.3%).

$^1$H-NMR (300 MHz, CDCl$_3$): ppm 0.00 (s, 3H), 0.39-0.53 (m, 2H), 1.5-1.6 (m, 2H), 3.25-3.43 (m, 2H), 3.52-3.78 (m, 14H), 4.17-4.3 (m, 2H), 5.7-5.85 (d, 1H), 6.0-6.2 (m, 1H), 6.3-6.45 (d, 1H).

Example 5

Synthesis of tetramethyl tetra(ethoxyacrylate) cyclotetrasiloxane (D4A, n=5)

18.1 g of D4-2,4,6,8-tetra(ethoxyethanol) (D4OE, n=5) was prepared in the same manner as in Example 1, except that 4 g of 2,4,6,8-tetramethylcyclotetrasiloxane (D4H) and 18.34 g of penta(ethylene glycol) monoallyl alcohol were used (yield=83.3%).

$^1$H-NMR (300 MHz, CDCl$_3$): ppm 0.00 (s, 3H), 0.39-0.43 (m, 2H), 1.50-1.62 (m, 2H), 2.7 (s, 1H), 3.31-3.47 (m, 2H), 3.5-3.8 (d, 20H)

15 g of tetramethyl tetra(ethoxyacrylate) cyclotetrasiloxane (D4A, n=5) was prepared in the same manner as in Example 1, except that 18 g of D4-2,4,6,8-tetra(ethoxyethanol) (D4OE, n=5) and 7.2 g of acryloyl chloride were used (yield=60%).

$^1$H-NMR (300 MHz, CDCl$_3$): ppm 0.00 (s, 3H), 0.39-0.53 (m, 2H), 1.5-1.6 (m, 2H), 3.25-3.43 (m, 2H), 3.52-3.78 (m, 18H), 4.17-4.3 (m, 2H), 5.7-5.85 (d, 1H), 6.0-6.2 (m, 1H), 6.3-6.45 (d, 1H).

Experimental Example 1

Ion Conductivity

1. Ion Conductivity at Various Lithium Salt Contents

Ion conductivity of a polymer electrolyte composition was measured at various concentrations of lithium salt (lithium trifluoromethanesulfonate, LiCF$_3$SO$_3$). The polymer electrolyte composition comprised D4A as a crosslinking agent, poly(ethylene glycol) dimethyl ether (PEGDMe 250, $M_w$=250) as a plasticizer, LiCCF$_3$SO$_3$ as lithium salt, and benzoyl peroxide (BPO) as a curing initiator.

The composition was poured onto a band-type conductive glass plate or a lithium-copper foil and was sufficiently polymerized by thermal-curing. After sufficient drying, AC impedance between the band-type or sandwich-type electrodes was measured under argon atmosphere. The result of the measurement was analyzed with a frequency response analyzer to find out the complex impedance. The band-type electrode was prepared in advance by attaching masking tapes of about 1 mm width on the center of conductive glass (ITO) at intervals of about 2 cm, etching with an etching solution, followed by washing and drying.

Ion conductivities at various concentrations of the lithium salt are given in Table 1 below.

TABLE 1

| Crosslinking agent (g) D4A (n = 4) | Plasticizer (g) PEGDMe250 | Lithium salt (g) LiCF$_3$SO$_3$ | Curing initiator (g) BPO | Ion conductivity (S/cm) $\sigma \times 10^{-4}$ |
|---|---|---|---|---|
| 0.2 | 0.2 | 0.0352 | 0.006 | 0.96 |
| 0.2 | 0.2 | 0.0441 | 0.006 | 1.3 |
| 0.2 | 0.2 | 0.0588 | 0.006 | 2.0 |
| 0.2 | 0.2 | 0.0882 | 0.006 | 3.9 |
| 0.2 | 0.2 | 0.1764 | 0.006 | 2.8 |

2. Ion conductivity with Different Plasticizers

Electrolyte films were prepared using the same crosslinking agent, lithium salt and curing initiator as above (i.e., D4A(n=4), LiCF$_3$SO$_3$ and BPO) and using PEGDMe 250 or a 1:1 mixture solution of ethylene carbonate (EC) and propylene carbonate (PC) as a plasticizer. Ion conductivity measurement was made at room temperature. The result is given in Tables 2 and 3 below.

TABLE 2

| Crosslinking agent (g) D4A (n = 4) | Plasticizer (g) | Lithium salt (g) LiCF$_3$SO$_3$ | Curing initiator BPO(g) | Ion conductivity (S/cm) |
|---|---|---|---|---|
| 0.1 | PEGDMe250 | 0.1 | 0.022 | 0.003 | 3.76 × 10$^{-4}$ |
| 0.1 | | 0.29 | 0.042 | 0.003 | 5.11 × 10$^{-4}$ |
| 0.1 | | 0.49 | 0.065 | 0.003 | 6.35 × 10$^{-4}$ |

TABLE 3

| Crosslinking agent (g) D4A (n = 4) | Plasticizer (g) | Lithium salt (g) LiPF$_6$ | Curing initiator BPO(g) | Ion conductivity (S/cm) |
|---|---|---|---|---|
| 0.70 | EC/PC = 1:1 | 0.30 | 0.045 | 0.021 | 5.90 × 10$^{-4}$ |
| 0.50 | | 0.50 | 0.076 | 0.015 | 33.0 × 10$^{-4}$ |
| 0.30 | | 0.70 | 0.106 | 0.009 | 52.3 × 10$^{-4}$ |

Electrolyte films were prepared using the same crosslinking agent, lithium salt and curing initiator as above (i.e., D4A (n=4), LiCF$_3$SO$_3$ and BPO) and using PSi-PEG (p=3) or D4-PEG (p=5) illustrated below, which are siloxane-based plasticizers, as a plasticizer. Ion conductivity measurement was made at room temperature. The result is given in Tables 4 and 5 below.

PSi-PEG (p = 3)

D4-PEG (p = 5)

TABLE 4

| Crosslinking agent (g) D4A (n = 4) | Plasticizer (g) | Lithium salt (g) LiCF$_3$SO$_3$ | Curing initiator BPO(g) | Ion conductivity (S/cm) |
|---|---|---|---|---|
| 0.1 | PSi-PEG | 0.1 | 0.025 | 0.003 | 2.1 × 10$^{-5}$ |
| 0.1 | (p = 3) | 0.29 | 0.049 | 0.003 | 3.2 × 10$^{-5}$ |
| 0.1 | | 0.49 | 0.074 | 0.003 | 5.0 × 10$^{-5}$ |

TABLE 5

| Crosslinking agent (g) D4A (n = 4) | Plasticizer (g) | Lithium salt (g) LiCF$_3$SO$_3$ | Curing initiator BPO(g) | Ion conductivity (S/cm) |
|---|---|---|---|---|
| 0.1 | D4-PEG | 0.1 | 0.022 | 0.003 | 4.8 × 10$^{-5}$ |
| 0.1 | (p = 5) | 0.29 | 0.042 | 0.003 | 5.6 × 10$^{-5}$ |
| 0.1 | | 0.49 | 0.065 | 0.003 | 6.5 × 10$^{-5}$ |

3. Ion Conductivity with Different Crosslinking Agents

Ion conductivity was measured at room temperature in the same manner as above, using D4A (n=1, 2, 4, 5), PEGDMe 250, LiCF$_3$SO$_3$ and BPO respectively as a crosslinking agent, plasticizer, lithium salt and curing initiator. The result is given in Tables 6, 7, 8 and 9 below.

Figure 1:
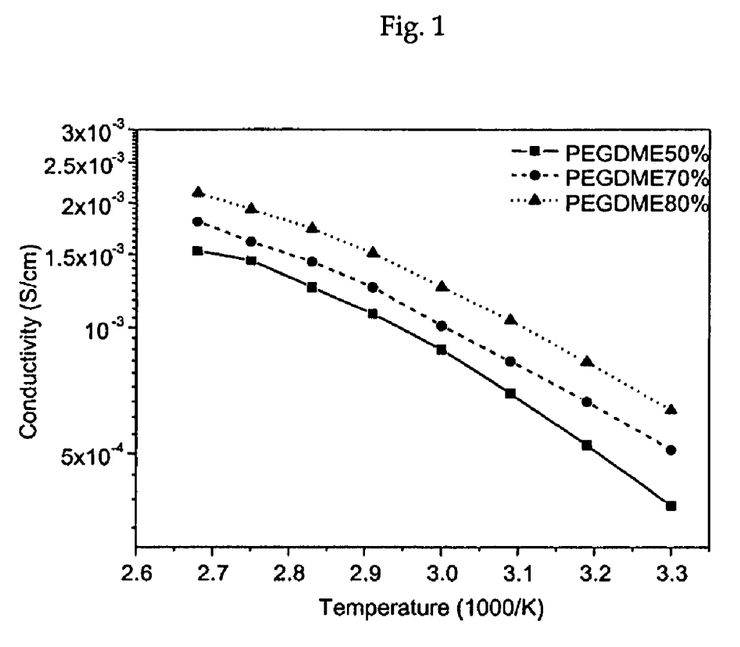
FIG. 1 is a graph showing the temperature-dependence of ion conductivity of a solid polymer electrolyte wherein D4A (n=3) was used as a crosslinking agent and PEGDMe 250 was used as a plasticizer.
Figure 2:
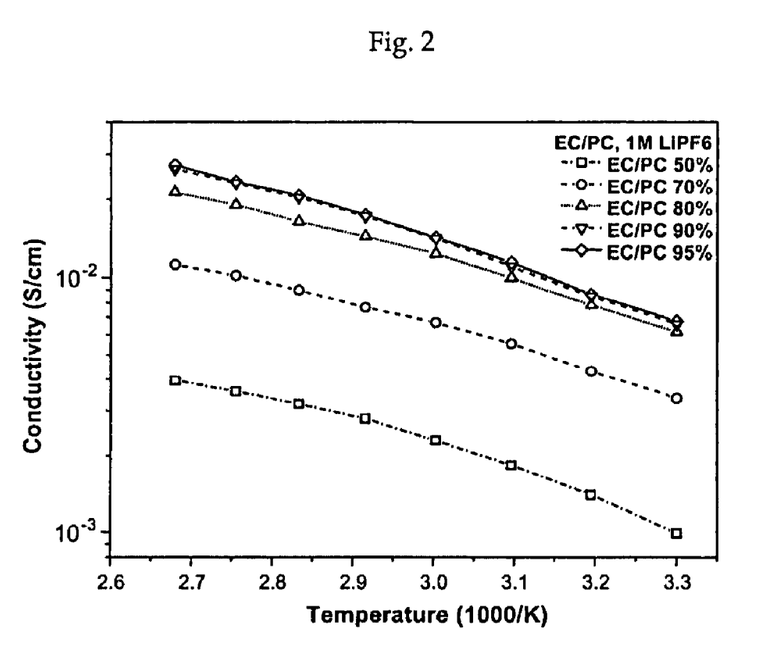
FIG. 2 is a graph showing the temperature-dependence of ion conductivity of a solid polymer electrolyte wherein D4A (n=1) was used as a crosslinking agent and an EC/PC mixture was used as a plasticizer.

Ion conductivity measurement was made by changing only the crosslinking agent to D4A (n=3). The result is given in FIG. 1. Ion conductivity measurement was made using D4A (n=1) as a crosslinking agent and changing the plasticizer from PEGDMe 250 to EC/PC. The result is given in FIG. 2.

TABLE 6

| Crosslinking agent (g) D4A (n = 1) | Plasticizer (g) PEGDMe250 | Lithium salt (g) LiCF$_3$SO$_3$ | Curing initiator BPO(g) | Ion conductivity (S/cm) |
|---|---|---|---|---|
| 0.1 g | 0.1 g | 0.0179 | 0.003 g | 2.72 × 10$^{-4}$ |
| 0.1 g | 0.29 g | 0.0380 | 0.003 g | 3.60 × 10$^{-4}$ |
| 0.1 g | 0.49 g | 0.0610 | 0.003 g | 6.55 × 10$^{-4}$ |

TABLE 7

| Crosslinking agent (g) D4A (n = 2) | Plasticizer (g) PEGDMe250 | Lithium salt (g) LiCF$_3$SO$_3$ | Curing initiator BPO(g) | Ion conductivity (S/cm) |
|---|---|---|---|---|
| 0.1 g | 0.1 g | 0.020 g | 0.003 g | 1.96 × 10$^{-4}$ |
| 0.1 g | 0.29 g | 0.040 g | 0.003 g | 4.38 × 10$^{-4}$ |
| 0.1 g | 0.49 g | 0.063 g | 0.003 g | 9.11 × 10$^{-4}$ |

TABLE 8

| Crosslinking agent (g) D4A (n = 3) | Plasticizer (g) PEGDMe250 | Lithium salt (g) LiCF$_3$SO$_3$ | Curing initiator BPO(g) | Ion conductivity (S/cm) |
|---|---|---|---|---|
| 0.1 g | 0.1 g | 0.023 | 0.003 g | 3.14 × 10$^{-4}$ |
| 0.1 g | 0.29 g | 0.043 | 0.003 g | 5.17 × 10$^{-4}$ |
| 0.1 g | 0.49 g | 0.066 | 0.003 g | 7.20 × 10$^{-4}$ |

TABLE 9

| Crosslinking agent (g) D4A (n = 5) | Plasticizer (g) PEGDMe250 | Lithium salt (g) LiCF$_3$SO$_3$ | Curing initiator BPO(g) | Ion conductivity (S/cm) |
|---|---|---|---|---|
| 0.1 g | 0.1 g | 0.024 | 0.003 g | 3.1 × 10$^{-4}$ |
| 0.1 g | 0.29 g | 0.044 | 0.003 g | 5.8 × 10$^{-4}$ |
| 0.1 g | 0.49 g | 0.067 | 0.003 g | 7.5 × 10$^{-4}$ |

Experimental Example 2

Electrochemical Stability

A solid polymer electrolyte film was prepared on a nickel electrode measuring 1 cm×1 cm in the same manner as above, using D4A (n=3) as a crosslinking agent and 50 wt % PEGDMe as a plasticizer. The resulting film was sandwiched between metallic lithium and vacuum sealed with a metalized polymer bag to prepare a cell for electrochemical stability measurement. Electrochemical stability was measured in the potential range from −0.3 to 5.5 V by linear sweep voltammetry at a scan rate of 5 mV/sec. The result is given in FIG. 3.

Figure 3:
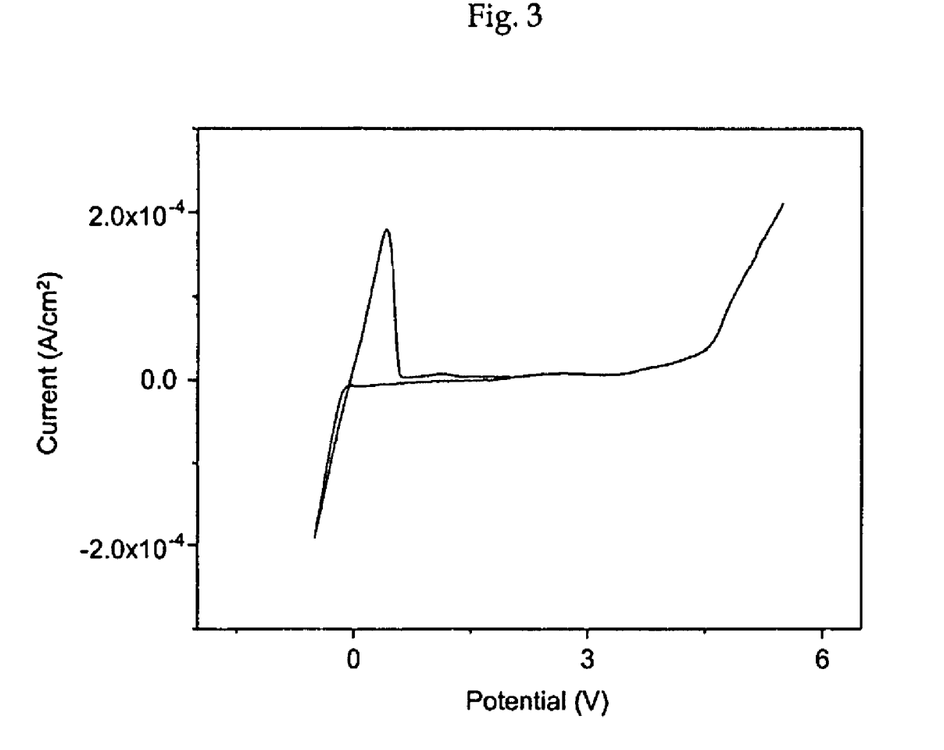
FIG. 3 is a graph showing the electrochemical stability of a solid polymer electrolyte measured by scanning voltammetry wherein D4A (n=3) was used as a crosslinking agent and PEGDMe 250 was used as a plasticizer.

Reversible oxidation-reduction of lithium was observed in the potential range of from −0.5 to 0.2 V. Oxidative degradation of the electrolyte was not observed below 4.6 V. That is, the polymer electrolyte of the present invention was electrochemically stable up to 4.6 V when lithium used as a reference electrode. Therefore, it was confirmed that the polymer electrolyte of the present invention has a sufficient electrochemical stability for use as a polymer electrolyte in lithium-polymer batteries.

Industrial Applicability

The novel cyclic siloxane-based compound of the present invention obtained by introducing polyalkylene oxide acrylate groups at the cyclic methyl siloxane side chain can be used as a crosslinking agent in a variety of fields, to improve mechanical strength, such as hardness and elasticity or increase chemical and electrochemical stabilities of polymer materials such as rubber and plastics.

In addition, the solid polymer electrolyte composition comprising the cyclic siloxane-based compound has improved compatibility with the plasticizer, which is added for improving ion conductivity of the electrolyte, due to the polyalkylene oxide groups introduced at the side chain. Moreover, the polymer electrolyte can have a 3-dimensional network structure by the introduction of acryl groups. The solid polymer electrolyte of the present invention is easily formed into thin films and, is thus useful as an electrolyte film for small-sized lithium-polymer secondary batteries used in cellular phones, notebook computers and PDA's and camcorders. Further, it can be used in high-capacity lithium-polymer secondary batteries used for power storage devices and electric vehicles. While the present invention has been described in detail with reference to the preferred embodiments, those skilled in the art will appreciate that various modifications and improvements can be made thereto without departing from the spirit and scope of the present invention as set forth in the appended claims.

The invention claimed is:

1. A solid polymer electrolyte composition comprising:

0.1-95 wt % of a cyclic siloxane-based crosslinking agent represented by the formula (1) below;

0.1-98 wt % of at least one plasticizer selected from the group consisting of polyalkylene glycol dialkyl ether represented by the formula (2) below, polymethyl(polyalkylene oxide)siloxane represented by the formula (3) below, methyl(polyalkylene oxide) cyclic siloxane represented by the formula (4) and a non-aqueous polar solvent;

3-40 wt % of lithium salt; and 0.1-5 wt % of a curing initiator:

(1)

(2)

(3)

wherein $R_1$, $R_2$ and $R_3$ are independently hydrogen or $C_1$-$C_6$ alkyl; $R_4$ and $R_5$ are independently $C_1$-$C_{10}$ linear or branched alkyl; $R_6$, $R_7$ and $R_8$ are independently hydrogen or methyl, n and m are independently an integer of from 0 to 20 (except when both n and m are 0); o, p and q are independently an integer of from 0 to 20 (except when both p and q are 0); and x is an integer of from 1 to 1000.

2. A solid polymer electrolyte film prepared by coating the solid polymer electrolyte composition as set forth in claim 1.

3. A solid polymer electrolyte for a small-sized lithium-polymer secondary battery comprising the solid polymer electrolyte composition as set forth in claim 1.

4. A solid polymer electrolyte for a high-capacity lithium-polymer secondary battery comprising the solid polymer electrolyte composition as set forth in claim 1.

* * * * *